(12) United States Patent
Martin (10) Patent No.: US 7,263,898 B1
(45) Date of Patent: Sep. 4, 2007

(54) FIXTURE FOR HOLDING A GEAR

(75) Inventor: Jeffrey D. Martin, Troy, OH (US)

(73) Assignee: Honda Motor Co., Ltd., Tokyo (JP)

( * ) Notice: Subject to any disclaimer, the term of this patent is extended or adjusted under 35 U.S.C. 154(b) by 499 days.

(21) Appl. No.: 10/994,433

(22) Filed: Nov. 22, 2004

(51) Int. Cl.
*G01N 3/02* (2006.01)

(52) U.S. Cl. ..................................... 73/856

(58) Field of Classification Search .......... 73/856–860
See application file for complete search history.

(56) References Cited

U.S. PATENT DOCUMENTS

| | | |
|---|---|---|
| 1,890,923 A | 12/1932 | Wilson |
| 2,804,769 A | 9/1957 | Clark, Sr. |
| 3,128,621 A | 4/1964 | Scott |
| 3,138,951 A | 6/1964 | Scott |
| 4,312,220 A | 1/1982 | Borgersen et al. |
| 4,361,034 A | 11/1982 | Borgersen et al. |
| 4,389,140 A * | 6/1983 | Bordes ............... 405/195.1 |
| 4,635,471 A | 1/1987 | Rogers et al. |
| 6,332,364 B1 | 12/2001 | Buschmann et al. |
| 6,533,355 B2 * | 3/2003 | Broekhuis et al. ......... 297/353 |
| 2002/0140266 A1 * | 10/2002 | Broekhuis et al. ......... 297/353 |
| 2003/0196480 A1 | 10/2003 | Anderberg |
| 2004/0096093 A1 | 5/2004 | Hauck et al. |
| 2004/0111970 A1 * | 6/2004 | Fenelon ................ 49/349 |

* cited by examiner

*Primary Examiner*—Jewel Thompson
(74) *Attorney, Agent, or Firm*—Rankin, Hill, Porter & Clark LLP; Vincent Ciamacco (57) ABSTRACT

A gear holding fixture is provided so that the appropriate position upon a gear tooth may be placed in line with an indenting device on testing equipment. The fixture includes a base that supports a movable rack, the rack including a plurality of teeth. The gear being tested is supported upon the movable rack in a way wherein the teeth on the gear intermesh with the teeth on the rack. The fixture also includes a gear axle restraint that is selectively movable depending on whether the gear is being tested or being replaced. The gear axle restraint in a gear testing position abuts an axle that supports the gear and extends along the gear's axis of rotation. This reduces the gear to only rotational movement. Thus, as the rack is moved incrementally along the base, the teeth on the rack drive the teeth of the gear, causing the gear to rotate.

17 Claims, 7 Drawing Sheets

FIXTURE FOR HOLDING A GEAR

BACKGROUND OF THE INVENTION

Gears are used in many mechanical applications including motor vehicles. The gear's teeth are critical areas, subject to the most wear as well as having the greatest propensity to fracture or otherwise fail. It is important that gears are designed to appropriate specifications to avoid such failure, including material size and material quality specifications.

One specific material quality important to wear and strength of the gear teeth is hardness. Each gear material has a usual hardness factor, but this may be changed by additional treatment of the material, either locally (i.e. to wear surfaces) or throughout the gear. The usual hardness or the amended hardness of the gear is often tested for accuracy and consistency. A number of hardness tests and apparatus have been developed, most involving the concept of applying multiple loads at a common position using a device that creates a small depression on the material surface. The difference in indentation depth between a minor load applied and a major load applied is reflective of material hardness.

The gear or other workpiece must be placed in a stable position that allows the indenting portion of a testing device to access the desired area, and to apply the load repeatedly. The gear or other workpiece must be held so as not to be moved by the application of the minor or major load. U.S. Pat. No. 2,712,754 illustrates a typical fixture used to hold a gear or gear-like object in a position for access by a hardness testing device. Specifically, two wedges engage teeth on generally opposite sides of the gear for support. However, fine adjustments are made using a slidable supporting foot and the degree of adjustment is limited.

What is desired is a gear holding fixture that allows for easy adjustment of the position of the gear, thus, allowing hardness testing to be carried out.

BRIEF SUMMARY OF THE INVENTION

The present invention overcomes these and other disadvantages in the prior art. The gear holding fixture of the present invention provides an easily adjustable device so that the appropriate position upon a gear tooth may be placed in line with an indenting device on testing equipment.

In accordance with the present invention, the fixture includes a base that supports a movable rack, the rack including a plurality of teeth. The gear being tested is supported upon the movable rack such that the teeth on the gear intermesh with the teeth on the rack. Thus, as the rack is moved, the teeth on the rack drive the teeth of the gear, causing the gear to rotate.

The fixture also includes a gear axle restraint that is selectively movable depending on whether the gear is being tested or being replaced and may be adjusted for gears having different diameters. The gear axle restraint in a first or gear testing position abuts an axle that supports the gear and extends along the gear's axis of rotation. This limits the gear to only rotational movement. In a second or loading/unloading position, the gear axle restraint is moved away from the axle of the gear. The gear may then be removed from the fixture. The gear axle restraint is affixed to a pair of glides which in turn are slidingly engaged with two contoured guides. The guides are each affixed to one of two posts that are in turn affixed to the fixture base. When in the first or test position, the gear is moved into a position of proper alignment by using a crank and screw that, when turned, move the rack incrementally along the surface of the fixture base.

These and other features, aspects and advantages of the present invention will be fully described by the following description, appended claims, and accompanying drawings.

DETAILED DESCRIPTION OF THE INVENTION

Figure 1:
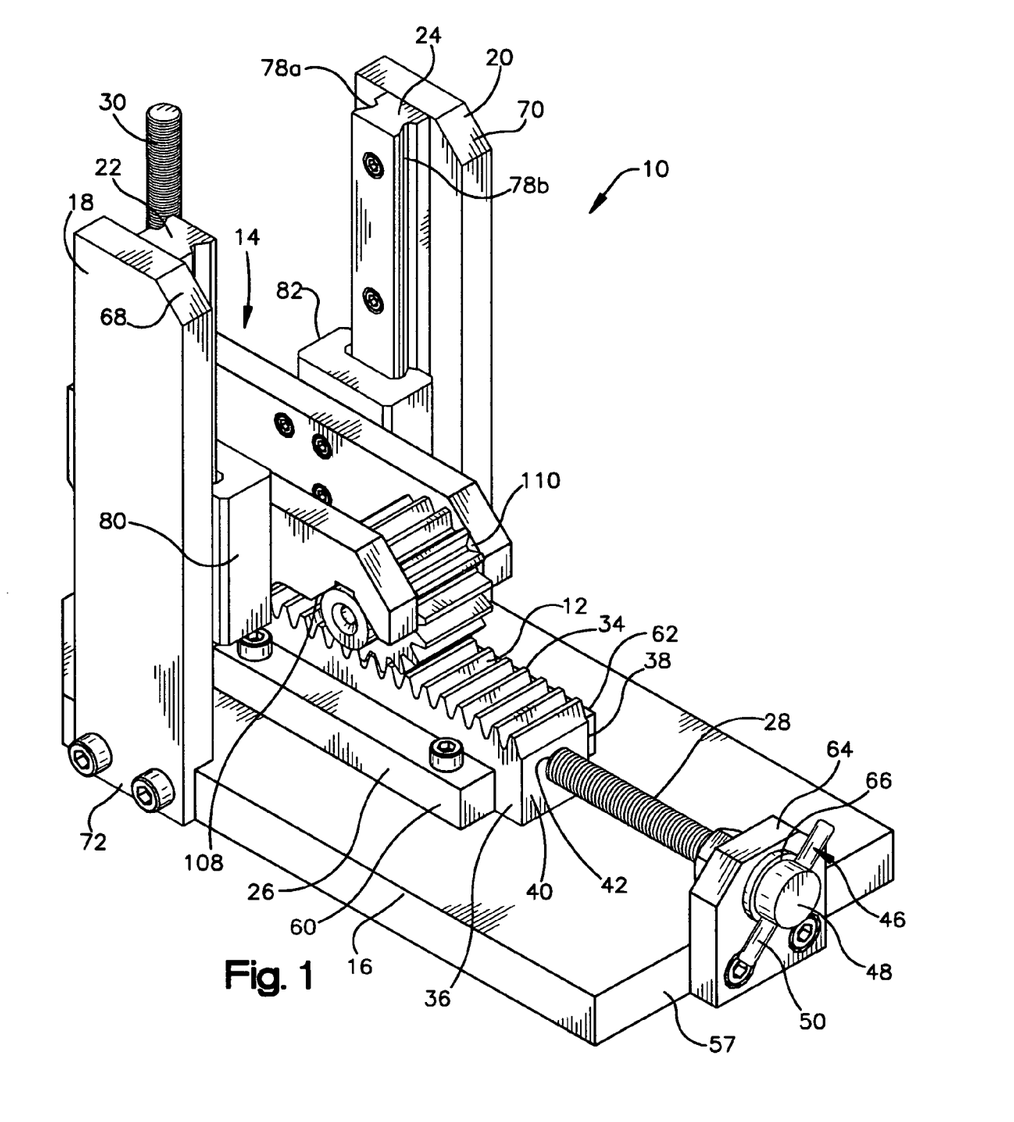
FIG. 1 is a first perspective view of the gear holding fixture of the present invention.
Figure 2:
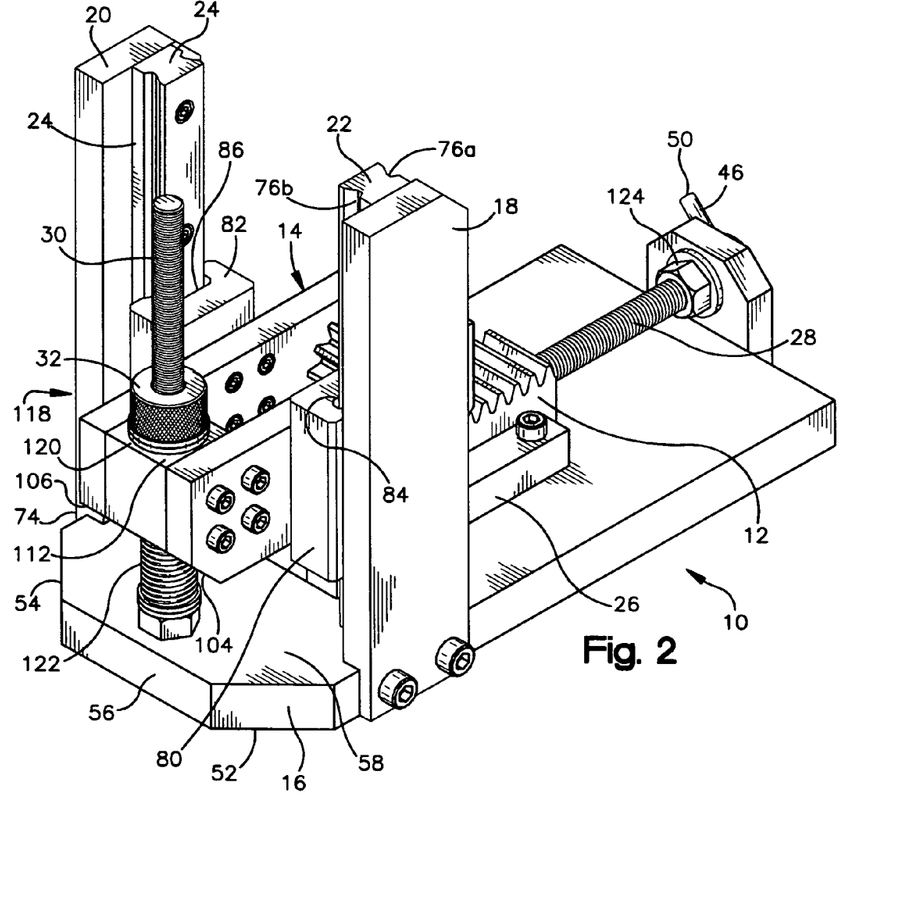
FIG. 2 is a second perspective view of the gear holding fixture of the present invention.
Figure 3:
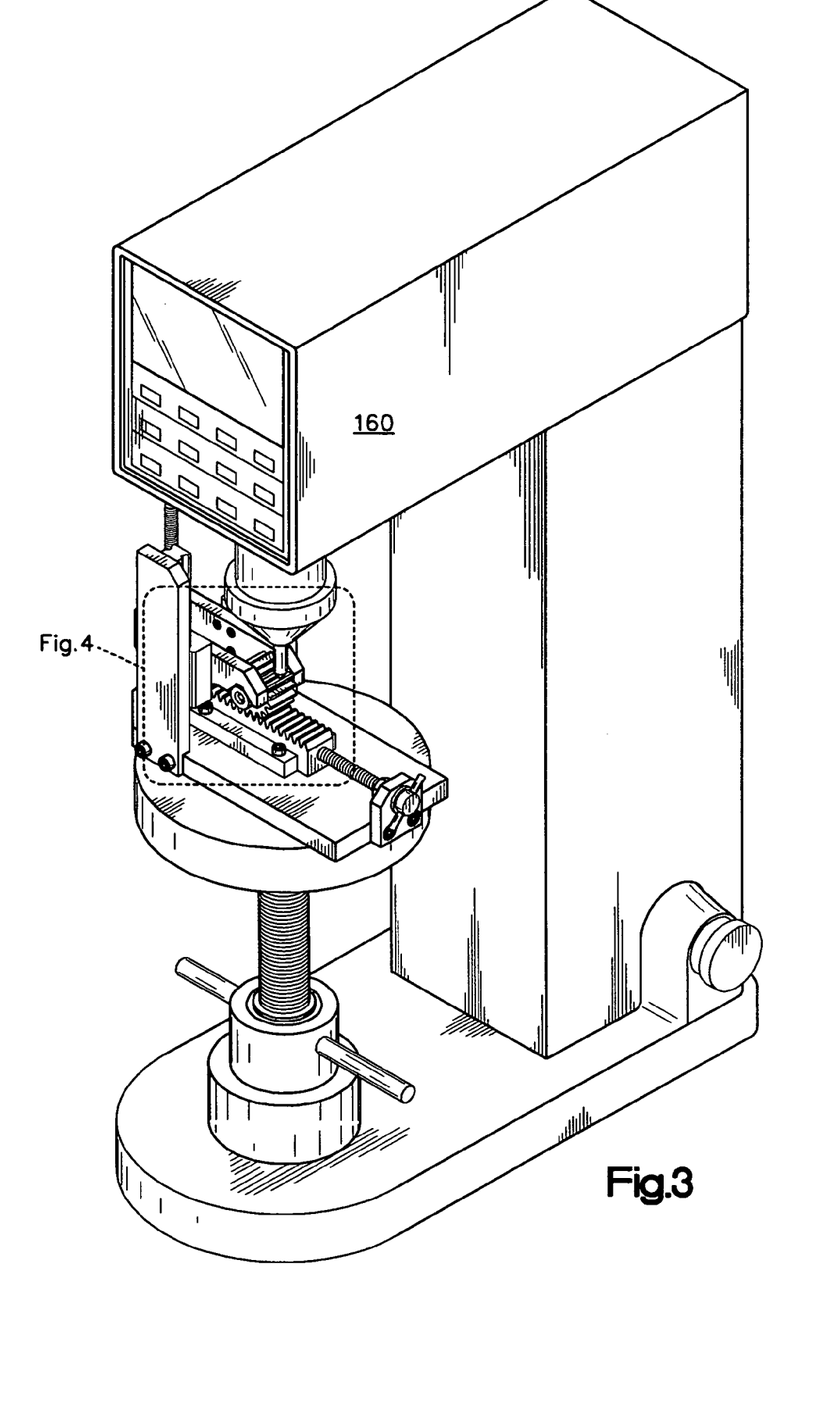
FIG. 3 is a front elevational view of the gear holding fixture oriented within a hardness testing apparatus.

Referring to the drawings, specifically FIGS. 1 and 2, a preferred gear holding fixture 10 according to the present invention is illustrated. The gear holding fixture 10 includes an adjustable rack 12 and adjustable gear axle restraint 14 that allow different sized gears to be secured and the gear's tooth position to be easily adjusted. As described in more detail below, the fixture 10 additionally includes a base 16, two posts 18, 20 including guides 22, 24, a gib 26, a translation screw 28 for moving the rack 12, and a threaded member 30 and thumb nut 32 for securing the gear axle restraint 14.

Referring to FIGS. 1 through 5, the rack 12 is formed from a generally rectangular plate have a plurality of teeth 34 protruding from an upper surface thereof. The teeth 34 are oriented transverse to the length of the rack 12. An opposite surface of the rack is smooth and slides across the upper surface of the base 16. The rack side surfaces 36, 38 perpendicular to the upper surface are also smooth and slide against the smooth surfaces of the gib 26. One end surface 40 of the rack 12 defines a threaded aperture 42 into which a translation screw 28 is threadingly received. The threaded aperture 42 has a sufficient depth to allow significant movement of the rack 12 with respect to the translation screw 28 which rotates, but does not move linearly. The opposite end surface 44 is smooth. Preferably, the rack teeth 34 have a uniform pitch matching the pitch of the gear being tested. Accordingly, different racks 12 will be required to test differently pitched gears.

The translation screw 28 is a threaded body extending lengthwise along the base 16. A crank 46 is affixed to an end of the translation screw 28 opposite the rack 12. The crank 46 includes a central barrel 48 and a t-handle 50 extending therethrough. The crank 46 is pinned or otherwise affixed to the screw 26 for common rotation therewith.

Referring to FIGS. 1 and 2, the base 16 slidingly supports the rack 12 and is a flat plate. The base 16 has a generally rectangular shape with two beveled corners 52, 54 at a first end 56. The gib 26 extends lengthwise along an upper face 58 of the base 16. The gib 26 comprises two rectangular blocks 60, 62 each defining two apertures, for facilitating attachment to the base 16. The blocks 60, 62 are spaced from one another so as to receive the rack 12 therebetween.

A mounting block 64, which is generally square in shape, is affixed to the second end 57 of the base 16. The mounting block 64 defines a central aperture 66 in a direction parallel to the length of the base 16 through which the translation screw 28 extends. A nut 124 is positioned adjacent to the mounting block 64 on a side adjacent to the rack 12. The central hole defined by the nut 124 is aligned with the central aperture 66 within the mounting block.

Two posts 18, 20 are shown extending perpendicular to a plane defined by the upper surface 58 of the base 16. The posts 18, 20 are generally rectangular in shape, and have one beveled corner at a first end 68, 70 opposite the base 16. The posts 18, 20 each define two apertures at a first end 72, 74 (adjacent the base) and three additional apertures along an imaginary central axis extending along the length of the posts 18, 20. The posts 18, 20 are affixed to the associated side surface of the base 16 by appropriate means, such as the illustrated screws or, optionally, by welding, etc.

Two guides 22, 24 extend parallel to the two rectangular posts 18, 20 and are affixed thereto. Each guide 22, 24 includes two notches 76a, 76b and 78a, 78b extending along the length of the guide 22, 24 on opposite sides, the sides being perpendicular to the face of the post 18, 20 to which the guide 22, 24 is affixed. Each guide 22 has a length that is generally equivalent to the length of a post 18 minus the thickness of the base 16. Each guide 22, 24 defines three apertures that facilitate attachment to the posts 18, 20 via mechanical fasteners.

Figure 5:
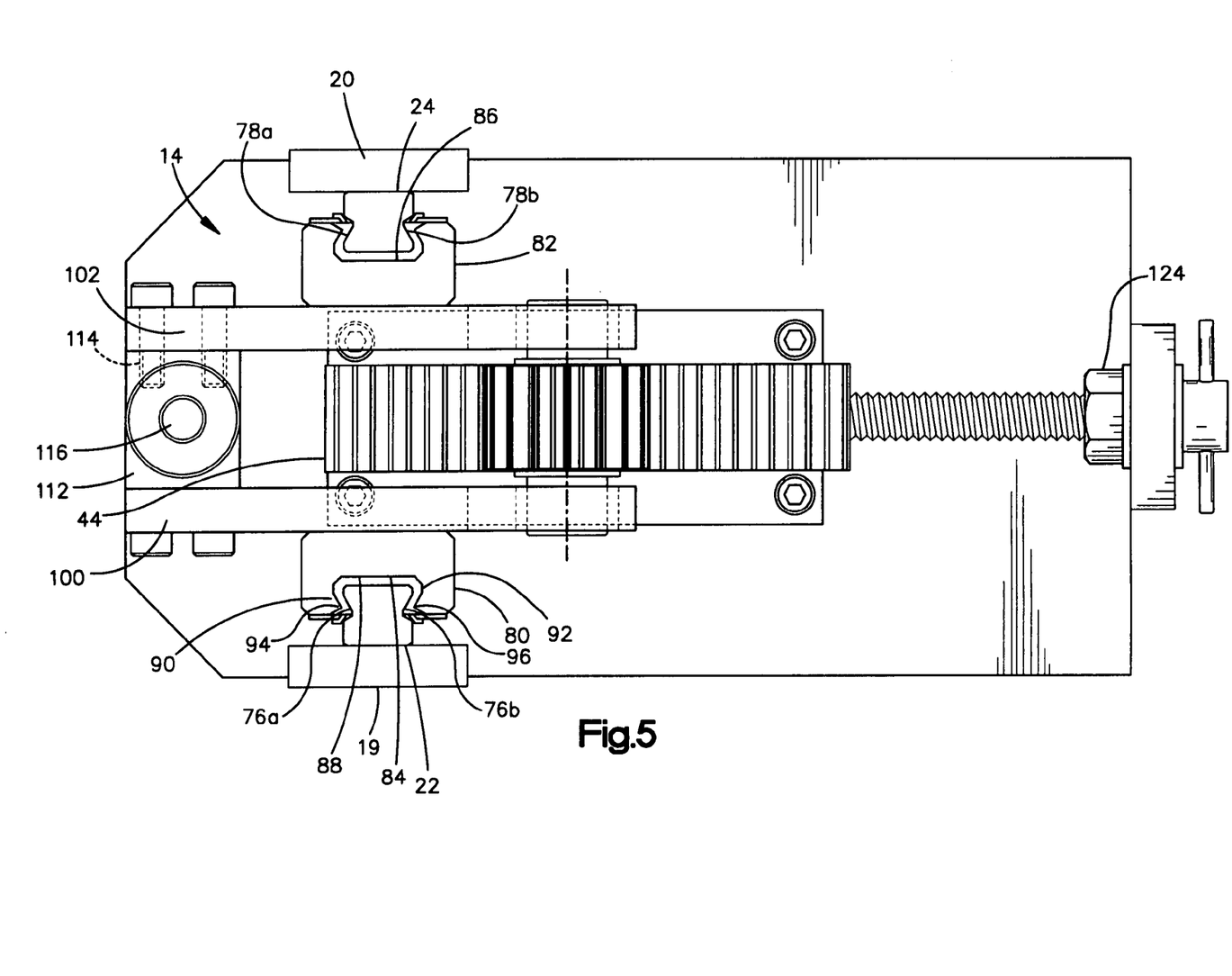
FIG. 5 is a top elevational view of a gear supported within the gear holding fixture of the present invention.
Figure 6:
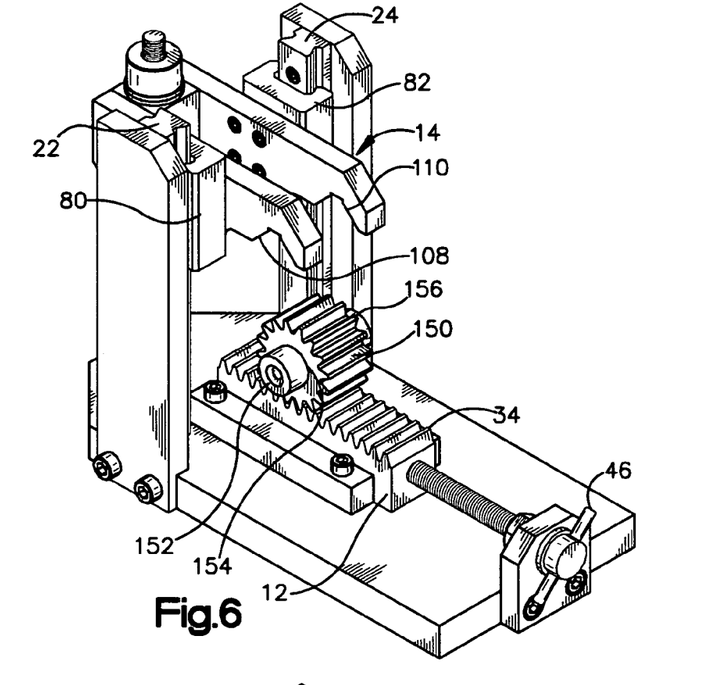
FIGS. 6-9 are perspective views showing the steps of loading a gear into the gear holding fixture.
Figure 7:
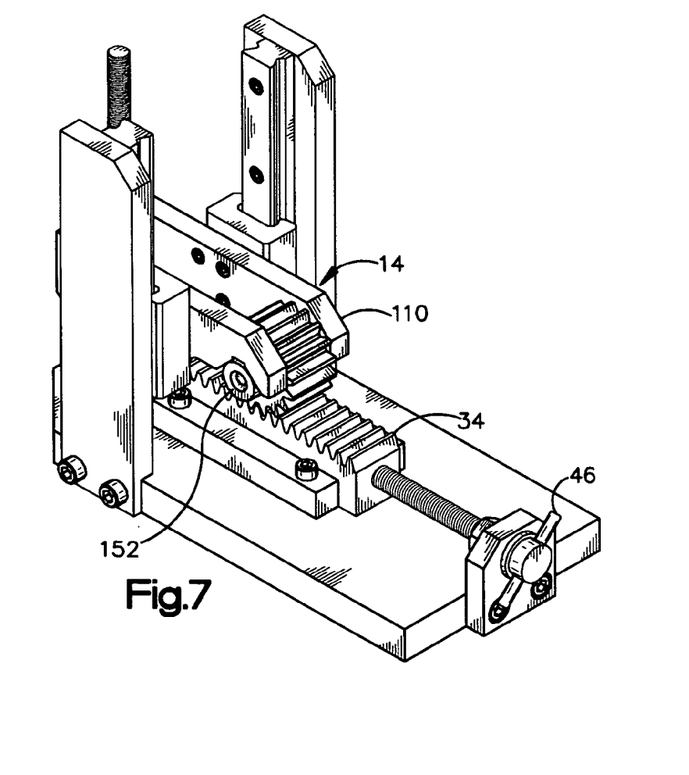
Figure 8:
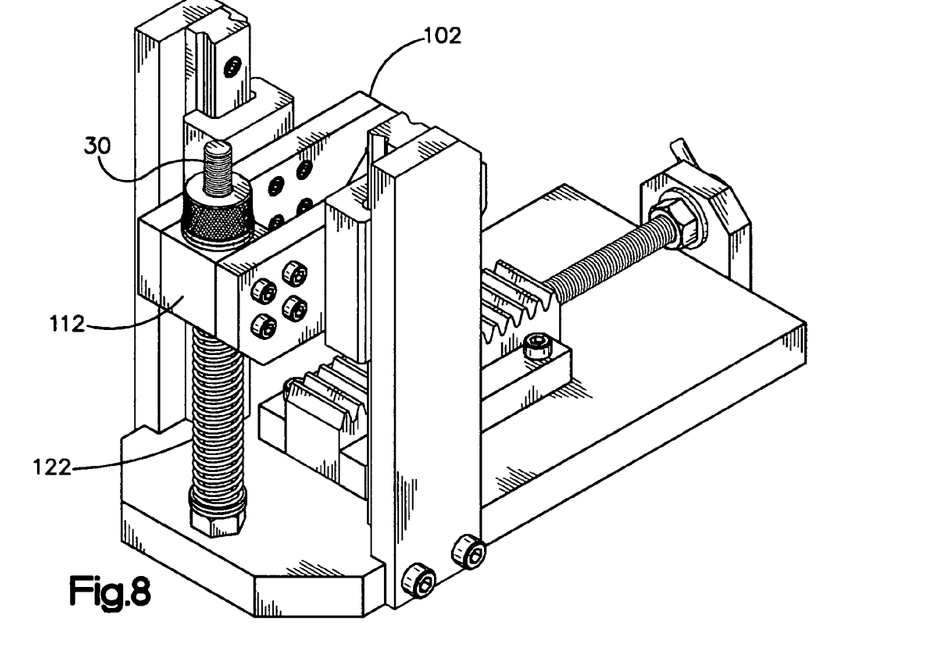
Figure 9:
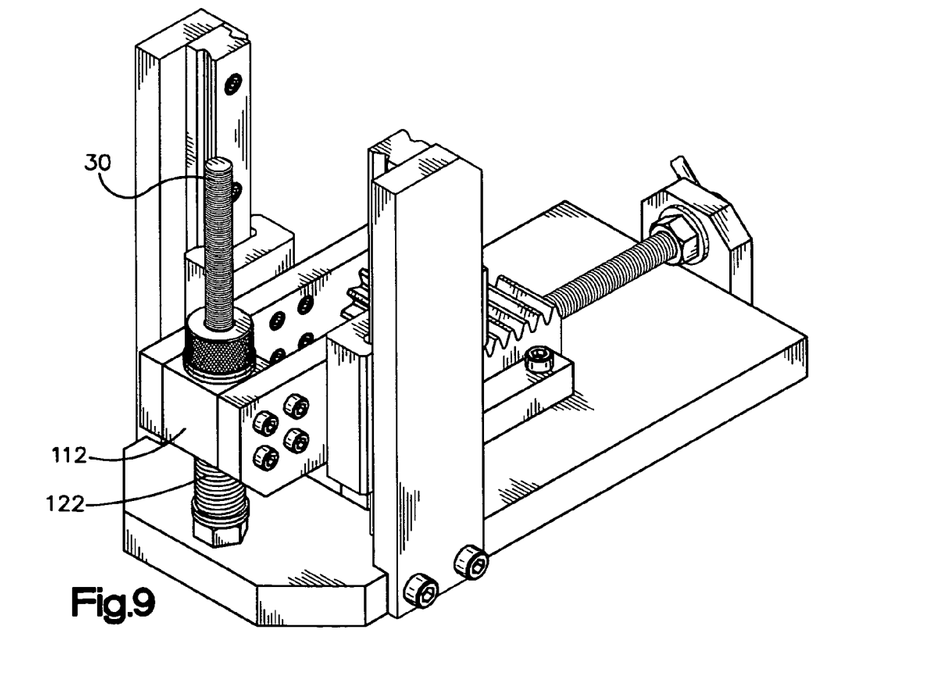

Referring to FIG. 5, each glide 80, 82 is a rectangular solid including a lengthwise extending channel 84, 86 on one side. The channel 84 on glide 80 includes a base wall 88 and two side walls 90, 92 and includes two lengthwise projections 94, 96, protruding from opposite channel side walls 90, 92. The projections 94, 96 have a shape that matches the inverse shape of the notches 76a, 76b on the guide 22. The channel 86 on glide 82 is generally identical to the channel 84 described hereinbefore.

Figure 4:
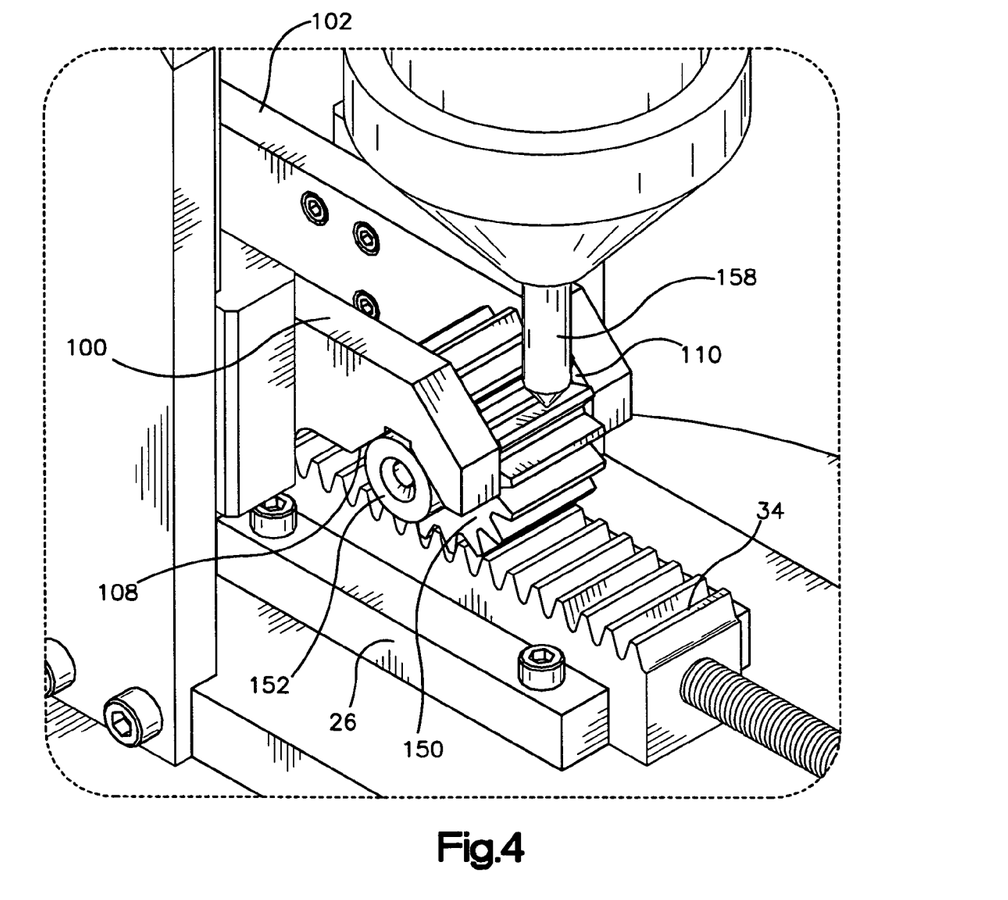
FIG. 4 is a perspective view of the gear holding fixture represented as a segment of FIG. 3.

Referring to FIGS. 2, 4 and 5, the gear axle restraint 14 includes two arms 100, 102, a base member 112, and an adjustment screw system 118. The arms 100, 102 extend lengthwise, parallel to, but laterally displaced from, the rack 12. Each arm 100, 102 is a generally rectangular solid with a height oriented parallel to the length of the posts 19, 20. Each arm 100, 102 may have a beveled corner 104, 106 at an end opposite the rack 12 and adjacent to the base 16. Each arm 100, 102 includes a V-notch section 108, 110 near the end closest to the rack 12. The notch 108, 110 is open downwardly so as to face toward the base 16. More specifically, the notch 108, 110 includes forward and rearward angled surfaces that are linked by a generally horizontal surface as illustrated. Each arm 100, 102 defines a plurality of apertures near the center of its length and at the end opposite the rack 12 to facilitate attachment to the base member 112 in a cantilever fashion.

The square base member 112 extends between and interconnects the arms 100, 102 at the end opposite the rack 12. The base member 112 defines a number of screw receptacles 114 and a central aperture 116 passing through the base member 112 in a direction perpendicular to the screw receptacles 114 and the arms 100, 102. Screws extend through apertures in the arms 100, 102 and into the screw receptacles 114 of the base member 112 to affix the arms to the base member.

The adjustment screw system 118 includes a threaded member 30, thumb nut 32, thrust washer 120 and compression spring 122. The threaded member 30 is oriented parallel to the posts 18, 20 and perpendicular to the base 16. One end of the threaded member 30 is supported by the base 16 at an end opposite the mounting block 64 and is located generally in the center of the base's width. Preferably, the threaded member 30 is threaded through a nut that is welded to the base, and into a threaded hole formed in the base to securely attach the threaded member 30 to the base 16. The threaded member 30 freely extends through the central aperture 116 defined by the base member 112.

The compression spring 122 fits over and around the threaded member 30 and is located between the base member 112 and the base 16. The thrust washer 120 and thumb nut 32 fit over the threaded member 30 and are located above the base member 112. The thumb nut 32 may have a knurled exterior making it easy to grip.

Referring to FIGS. 1, 2 and 5, the gib 26 (i.e., blocks 60, 62) is affixed to the upper face 58 of the base 16 lengthwise using screws. The rack 12 is supported on the base 16, between the gib 26 and is allowed to slidingly move, lengthwise along the base 16. The translation screw 28 is threaded into the aperture 42 in the end 40 of the rack 12. The opposite end of the translation screw 28 is threaded through the nut 124 and affixed thereto with a pin and passes freely through an aperture 66 in the mounting block 64. The crank 46 is affixed to the end of the translation screw 28 passing through the mounting block 64 using a pin. As the crank 46 is rotated the rack 12 slides lengthwise along the base 16.

The posts 18, 20 are bolted to sides of the base 16 and interior sides of the posts 18, 20 point toward the rack 12. Each guide 22, 24 is affixed to an interior side of one of the posts 18, 20. Preferably, an upper end of the guide 22, 24 is flush with the upper end of the associated post 18, 20, and the lower end of the guide abuts the base 16. Each guide 22, 24 is bolted to the post 18, 20 and is located in the center of the post's width. Each guide 22, 24 slidingly receives one of the glides 80, 82. The projections 94, 96 within the channel 84 defined by each glide 80, 82 fit within the notches 76a, 76b and 78a, 78b defined by the guides 22, 24. Each glide 22, 24 is affixed to one of the arms 100, 102 of the gear axle restraint 14, generally at a mid-point of the arm.

The gear axle restraint 14 is assembled by bolting each arm 100, 102 to an opposite side of the base member 112. Thus, the notches 108, 110 on the arms 100, 102 are aligned. The lower end of the threaded member 30 is affixed to the base 16 and the compression spring 122 is placed around the threaded member 30. The base member 112 of the gear axle restraint 14 is placed over the threaded member 30 which places the spring 122 between the upper surface of the base 16 and the lower surface of the base member 112. The aperture 116 within the base member 112 allows passage of the threaded member 30, but not the spring 122. The thrust washer 120 is placed over the threaded member 30 and against the upper side of the base member 112. The thumb nut 32 is threaded onto the threaded member 30 and, when tightened, abuts the thrust washer 120.

Referring to FIGS. 3-4 and 6-9, a gear 150 is selected for testing. If not already including a stub axle 152, one is chosen from a supply and is placed through a central aperture 154 within the gear 150. The operator determines how high the gear axle restraint 14 must be raised in order to allow the gear 150 to be placed in a position where the stub axle 152 is aligned with the notches 108, 110 in the arms of the gear axle restraint 14. The thumb nut 32 is rotated allowing the spring 122 to force the base member 112 and arms 100, 102 of the gear axle restraint 14 to the proper position. The base member 112 of the gear axle restraint 14 moves along the threaded member 30 and the glides 80, 82 move along the guides 22, 24 under the influence of spring force. The gear 150 is put in place with its teeth 156 intermeshed with teeth 34 upon the rack 12 and the stub axle 152 aligned with the notches 108, 110 on the arms 100, 102. The thumb nut 32 is then rotated in an opposite direction until the arms 100, 102 firmly secure the gear 150 in position. However, the gear 150 may still be rotated around its stub axle 152 via movement of the rack 12, described hereinafter.

The appropriate gear tooth 156 to be tested is chosen and the appropriate alignment of that gear tooth 156 is determined to access by the indenter 158 of the hardness tester 160. Generally, the selected gear tooth 156 is positioned so that the surface thereof being tested is substantially parallel to the base 16. The crank 46 is moved in either a clockwise or counter clockwise direction to rotate the gear 150 in the necessary direction to place the selected gear tooth in the desired orientation. Movement of the crank 46 causes the translation screw to rotate which in turn causes the rack 12 to move linearly. Preferably, no lock is used to hold the translation screw 28 in place during testing. Although force is applied to the gear during testing, it is not sufficient to rotate the translation screw 28 and, thus, cannot move the rack 12. Accordingly, application of testing forces will not cause the gear to rotate.

The gear 150 is now ready to be tested. If another tooth 156 on the same gear 150 needs to be tested, the gear 150 may be rotated to the appropriate position by turning the crank 46 that moves the rack 12. When testing is complete, the gear axle restraint 14 is loosened by rotation of the thumb nut 32. The gear axle restraint 14 may then be raised and the gear 150 removed from the fixture 10.

The posts are shown having a generally rectangular shape, but may be any shape such as rod-like or tubular. To assist in sliding the glides may be equipped with ball or roller bearings secured within a race. The adjustment screw system may be replaced with a pneumatic piston and return spring system. Both or either of the adjustment screw system and crank for moving the rack may be fitted with a stepper motor to allow precise incremental movements. The crank is described as including a T-handle, but may, alternatively, have a handle of any shape, such as a cylinder with a knurled outside surface.

The present invention is an improvement over the prior art because it is a compact, fully contained fixture with a flat bottom that may be placed within numerous different hardness testing devices. No loosening of bolts or other stops is required to rotated the gear for desired alignment. Additionally, a large degree of rotational adjustment is allowed due to the length of the rack.

Although the invention has been shown and described with reference to certain preferred and alternate embodiments, the invention is not limited to these specific embodiments. Minor variations and insubstantial differences in the various combinations of materials and methods of application may occur to those of ordinary skill in the art while remaining within the scope of the invention as claimed and equivalents.

What is claimed is:

1. A fixture for adjusting orientation of a gear in preparation for, and holding during, hardness testing comprising:
    a base having an upper surface;
    a linearly movable rack for providing adjustment, said rack being slidably supported on said base and including a plurality of gear engagement teeth;
    a gear restraint selectively movable in a direction generally perpendicular to said base between a gear testing position and a loading/unloading position.

2. The fixture of claim 1, wherein said gear restraint comprises two arms and a base member, said arms extending from said base member in a cantilever fashion.

3. The fixture of claim 1, further including a translation screw and a crank, said translation screw being received in said rack and cooperating with said crank to move said rack.

4. The fixture of claim 2, further including two posts extending perpendicularly from said base, said posts slidingly supporting said gear restraint.

5. The fixture of claim 4 further comprising two guides affixed to said posts and two glides, each glide being affixed to one of said arms and wherein said glides travel in sliding engagement within grooves in said guides.

6. A gear holding fixture in combination with a gear comprising:
    a gear supported on an axle;
    a rack, linearly movable in a direction perpendicular to the rotational axis of the gear, for supporting the gear, said rack including a plurality of gear engagement teeth; and
    a gear axle restraint movable relative to said gear and said rack between a gear testing position, in which the gear is secured between the rack and restraint, and a loading/unloading position, in which the gear may be removed from said rack.

7. The combination of claim 6, wherein said gear axle restraint comprises two arms and base member, said arms extending from said base member in a cantilever fashion.

8. The combination of claim 7, wherein each of said arms includes a V-notch section for receiving the axle supporting the gear.

9. The combination of claim 6, further including a gib for preventing movement of the rack in a direction parallel to the rotational axis of the gear.

10. The combination of claim 6, further including a translation screw and a crank, said translation screw being received in said rack and cooperating with said crank to move said rack.

11. The combination of claim 6, further including a base supporting said rack, said rack slidingly supported on an upper surface of said base and said gear axle restraint movable perpendicularly with respect to said upper surface of said base.

12. The combination of claim 11, further including two posts extending from said base, said posts slidingly supporting said gear axle restraint.

13. The combination of claim 12, further including two guides and two glides, each glide being affixed to one of said arms and when said glides travel in sliding engagement within grooves in said guides.

14. The combination of claim 7, further including:
    a base supporting said rack; and
    said restraint further comprising:
        a threaded member affixed to said base and passing through an aperture defined by said base member;
        a threaded member threadedly affixed to said threaded member on a side of the base member opposite the base; and
        a helical spring placed around the threaded member between the base member and base.

15. A method of preparing a gear for hardness testing and holding the gear during said testing comprising the steps of:
    supporting a gear upon a rack, said rack including a plurality of teeth, and intermeshing teeth upon the gear with said teeth of the rack;

securing said gear in place by closing an gear axle restraint over an axle supporting said gear; and moving said rack linearly by actuating a crank until a selected gear tooth on said gear is aligned with an indenter upon a hardness tester.

16. The method of gear preparation of claim 15 wherein the step of securing the gear in place includes turning a thumb screw to move a base member attached to two arms into engagement with said axle supporting said gear.

17. The method of gear preparation of claim 15 wherein the step of securing the gear in place includes moving said gear restraint toward said rack.

* * * * *